(12) United States Patent
Gore et al.

(10) Patent No.: US 6,218,673 B1
(45) Date of Patent: Apr. 17, 2001

(54) OPTICAL SCANNING TOMOGRAPHY FOR THREE-DIMENSIONAL DOSIMETRY AND IMAGING OF ENERGY FIELDS

(75) Inventors: John C. Gore; Marek J. Maryanski; Robert J. Schulz, all of Guildford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 08/927,572

(22) Filed: Sep. 5, 1997

Related U.S. Application Data (60) Provisional application No. 60/025,410, filed on Sep. 6, 1996.

(51) Int. Cl.[7] .................................................. G01T 1/02
(52) U.S. Cl. ................................... 250/474.1; 250/473.1
(58) Field of Search ........................... 250/474.1, 472.1, 250/473.1; 365/106

(56) References Cited

U.S. PATENT DOCUMENTS 5,319,210 * 6/1994 Moscovitch ........................ 250/474.1
5,633,584 * 5/1997 Maryanski et al. .................. 324/300

OTHER PUBLICATIONS

Audet, C., et al., ]995, Med. Phys. 22:951.
Gore, J.C., & Tofts, P.S., 1978, Phys. Med. Biol. 23:1176–1182.
Ibbott, G.S., et al., 1995, Med. Phys. 22:951.
Maryanski, M.J., et al., 1994, Med. Phys. Biol. 39:1437–1455.
Maryanski, M.J., et al., 1995, Med. Phys. 22: 950, 951.
Maryanski, M.J., et al., 1996, Med. Phys. 23:699–705.
Ramachadran, G.N., et al., 1971, P.N.A.S. USA 68:2236–2240.
Ranade, M., et al., 1995, Med. Phys. 22:1540.
Shepp, L.A., & Logan, B.F., 1974, IEEE Trans. Nucl. Sci. NS 21: 21–43.
Tofts, P.S., & Gore, J.C., 1980, Phys. Med. Biol. 25:117–127.
Wong, P.S., et al., 1995, Med. Phys. 22:951.

* cited by examiner

*Primary Examiner*—Seungsook Ham
*Assistant Examiner*—Richard Haniq
(74) *Attorney, Agent, or Firm*—Mary M. Krinsky (57) ABSTRACT

An optical scanner gives three dimensional dosimetric data by scanning, with at least one light beam, a translucent medium exhibiting optical properties which change upon receipt of radiant energy representing a dose distribution of the energy. At least one detector is employed to gather data indicative of changes in the optical properties of the medium after scanning from multiple directions to provide a representation of the optical properties in sections through the medium. Typical optical properties measured include optical density, light scattering, emitted light intensities, and combinations thereof. Methods of reconstructing a three-dimensional energy field as a series of two-dimensional images by applying an energy field to a translucent medium having distinct optical properties that change upon receipt of the energy field, optically scanning the translucent medium at various angles, detecting and measuring data indicative of optical changes in the medium, and preparing a two-dimensional image of the energy field by analyzing the changes in the optical properties are also provided.

20 Claims, 8 Drawing Sheets

OPTICAL SCANNING TOMOGRAPHY FOR THREE-DIMENSIONAL DOSIMETRY AND IMAGING OF ENERGY FIELDS

RELATED APPLICATION DATA

This application claims priority benefit of provisional U.S. application Ser. No. 60/025,410 filed Sep. 6, 1996.

STATEMENT REGARDING FEDERALLY SPONSORED RESEARCH

The invention was made with partial government support under grants CA40675 and CA49789 from the National Institutes of Health. The government has certain rights in the invention.

TECHNICAL FIELD

This invention relates to an optical tomographic system that permits the accurate reconstruction in a series of two-dimensional images of three-dimensional dose distributions or energy fields represented using polymer gels.

BACKGROUND OF THE INVENTION

It has been previously suggested (Maryanski, et al., 1994) that three-dimensional aspects of tissue-equivalent, polymer-gel dosimeters, combined with the flexibility and high resolution inherent in magnetic resonance imaging, can provide radiation dose distributions in a manner that is unique to the field of radiation oncology. Tomographic analysis of an irradiated polymer gel can yield important dosimetry data for the new and highly complex treatment modalities which are being introduced into radiation oncology such as stereotactic radiosurgery, conformal radiation therapy, the dynamic wedge, scanning electron beams and energy-modulated proton beams. While MRI will likely remain the method of choice at some institutions for specific types of studies, for many institutions there will be significant financial, administrative and logistical advantages to have a relatively low-cost tomographic dosimetry system located in the radiation oncology department which can readily provide the bulk of the clinical and research data required by the radiation oncology physicists.

SUMMARY OF THE INVENTION

It is an object of the invention to provide a tomographic system which accurately reconstructs three-dimensional energy fields as a series of two-dimensional images.

It is another object of the invention to provide a tomographic system of the above character which optically scans dose distributions represented in translucent media.

It is a further object of the invention to provide tomographic systems of the above character which are useful for the determination of three-dimensional dose distributions in irradiated translucent media, including measurements of the complex distributions produced by multi-leaf collimators, dynamic wedge and stereotactic treatments, and for quality-assurance procedures.

These and other objects are accomplished by the present invention, which provides an optical scanner for measuring three dimensional dosimetric data comprising a translucent medium exhibiting optical properties, e.g., optical density, light scattering, emitted light intensities, and combinations thereof, which change upon receipt of radiant energy representing a dose distribution of the energy; at least one light beam such as a laser beam or a series of divergent rays for scanning the translucent medium; and at least one detector, and in some embodiments, multiple detectors, for receiving and measuring data indicative of changes in the optical properties of the medium after scanning from multiple directions to provide a representation of the optical properties in sections through the medium. In the practice of the invention, the space accommodating the medium, a light source, mirrors to deflect beams, and/or a detector may be moved to provide scanning in multiple directions. One embodiment employs moving mirrors to deflect light beams.

In one embodiment, an optical scanner incorporates a He—Ne laser, photodiode detectors, and a rotating translucent media platform to measure dosimetric data stored within tissue-equivalent translucent media such as polymeric gels. Using mirrors mounted on a translating stage, the laser beam scans across the translucent media between each incremental rotation of the platform. Using the set of optical-density projections obtained, a cross-sectional image of the radiation field is then reconstructed. Doses in the range 0–10 Gy can be measured to better than 5% accuracy with a spatial resolution ≈2 mm.

The invention further provides a method of reconstructing a three-dimensional energy field as a series of two-dimensional images by applying an energy field to a translucent medium having distinct optical properties that change upon receipt of the energy field; optically scanning the translucent medium at various angles; detecting and measuring data indicative of optical changes such as those mentioned above in the medium; and preparing a two-dimensional image of the energy field by analyzing the changes in the optical properties. The depth of the translucent medium at which the optical scanning step occurs may be changed, and the optical scanning and detecting steps, repeated, to provide different two-dimensional images in the series. The two-dimensional images may be reviewed in consideration of altering or confirming radiant energy treatment.

DESCRIPTION OF THE FIGURES

FIG. 5 shows optically scanned two-dimensional dose distributions of irradiated polymer gels.

FIG. 6 shows cross sectional dose maps at three levels produced by optical scanning of a gel irradiated by a 4×4 cm 12 MeV electron beam.

DETAILED DESCRIPTION OF THE INVENTION

The principle employed for deriving dose distributions from changes in the optical density in a polymer gel is similar to that used in x-ray computed tomography, i.e., a planar image of an object is constructed from a series of line integrals obtained from projections taken from different directions. The intensity of a monochromatic light beam passing through the medium is attenuated exponentially under narrow beam conditions. If $\mu(x,y)$ denotes the optical attenuation coefficient per unit length in a section of the object, then the intensity exiting the sample at position x is $I(x)$ when the incident intensity is $I_0$ $$I(x)=I_0 e^{-\int \mu(x,y) dy}$$

Figure 1:
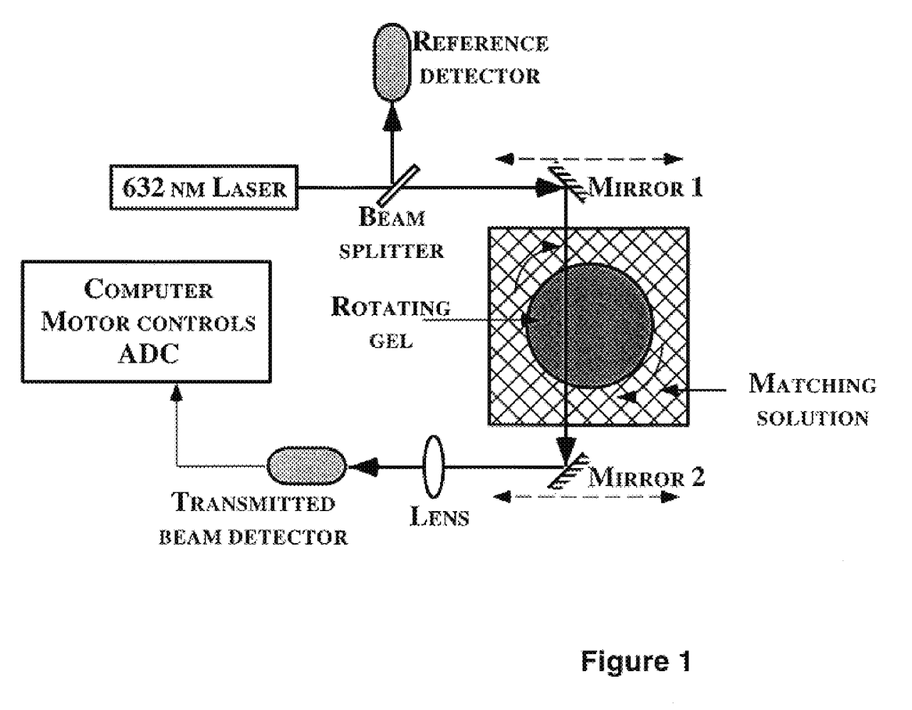
FIG. 1 is a schematic diagram of a scanner of the invention. The mirrors and/or optical stage translate left to right to obtain projections of the gel optical attenuation, as described in the text. Between each translation the gel is rotated by a second stepping motor.

A prototype scanning system has been constructed which provides optical-attenuation profiles of irradiated gels. A laser beam is scanned in a translate-rotate fashion to obtain projections of the gels from different angles, and these are then used to reconstruct the optical attenuation coefficient in a thin section through the gel. The device runs in automatic fashion under computer control, and the images are reconstructed using filtered back-projection on a Macintosh computer. A schematic that illustrates the operation of the prototype device is shown in FIG. 1.

The laser (He—Ne, 632 nm, 0.8 mw, Uniphase Inc., San Jose, Calif.) and large-area (1 cm$^2$) photodiode detectors (Hamamatsu) remain stationary during the scanning process. The output of the photodiodes are linearly amplified prior to digitization. The horizontal laser beam is first divided by a beam splitter and one beam is detected by one photodiode detector to provide a reference measurement of incident intensity. The second beam is then reflected through 90° by a mirror, and is then almost normally incident upon the flat, Lucite wall of a water tank which holds a cylindrical vessel containing the polymer gel. After transmission by the gel, the beam exits through the distal wall of the Lucite tank, is reflected through 90° by a second mirror, and is then collected by the second diode detector.

The mirrors are mounted on a carriage which can travel the length of the Lucite tank. The carriage is driven laterally by a computer-controlled stepping translational stage (Velmex Inc., Bloomfield, N.Y.). Scanning speeds for the prototype scanner are up to 20 cm/s, and the maximum scan length is 23 cm. As with CT scanners, the scanned length must be carefully centered at the point corresponding to the projection of the axis of rotation of the gel vessel. After each lateral scan, the vessel containing the gel is made to rotate through an adjustable, small angle (in preliminary studies, usually 2°–3°) by a computer-controlled stepping motor. The scan/rotate process is repeated until the vessel has been rotated through 180°. A short-focal-length lens in front of the diode detector corrects for any non-uniform response of the diode across its face by keeping the laser beam centered on the detector. In the first prototype, to change the depth of the plane to be scanned, the gel vessel is raised or lowered in the water tank in relation to the optical path of the laser beam, but additional mirrors may also be used to deflect the laser beam height and permit multislice scanning.

Data acquisition and the mechanical movements of the scanner are under the control of general purpose instrumentation control cards and software (Superscope 2 by GW Instruments Inc., Somerville, Mass.) which runs on a Power Mac computer. A 16-bit A/D card is used for data acquisition, and each sample point in each projection is obtained by averaging over a number of samples determined by the rate of linear translation. Typically, up to 1000 samples are averaged per point at a digitization rate of approximately 25 kHz, allowing 70 sampling points to be measured in 3 seconds. Unless otherwise noted, for the images described herein the lateral scan length was approximately 12 cm and the total data acquisition time for a 60×60 pixel image was 6 minutes.

After acquisition, the projection data are transferred to an image reconstruction program written using MathLab (The Math Works, Natick, Mass.). The logarithms of the projections are calculated and the program reconstructs a two-dimensional image of the distribution of optical density using the method of filtered back-projection with either the Shepp and Logan or Ram and Lak filters (Ramachandran and Lakshminarayanan, 1971; Shepp and Logan, 1974). Sub-routines that permit further processing, including smoothing, the analysis of regions of interest, and the delineation of isodose (isodensity) contours have also been implemented. No smoothing was used on the data presented herein.

One of the primary goals of this invention was to construct an optical scanning system in which the effects of refraction at interfaces are minimized and the need for software corrections to the raw data is small. To achieve this goal, it was first decided that the polymer-gel vessels would be cylindrical because cylinders are invariant when rotated about their axes, and because cylindrical vessels are readily fabricated from plastics such as Lucite. To avoid having the light beam scan to either the extreme right or left side of the cylinder (where it would be largely reflected), the width of the scanned area was restricted to less than the cylinder's full diameter. This constraint requires that the cylinders containing the polymer gel be irradiated through the ends, and that the radiation fields be no larger than about 90% the cylinder's diameter. In practice, the unirradiated gel is much more transparent than the irradiated portions, and so the incomplete projection data are almost identical to the complete data set. The measured data are extrapolated over the dimension not acquired to reduce residual edge artifacts. Second, to avoid refraction of the light beam which would occur at the entering and exiting surfaces of a cylindrical vessel supported in air, the vessel was placed in a rectangular tank filled with water. A light beam incident upon the side wall of this tank at a small angle from normal, so as to prevent back reflection, then enters and exits from this tank at the same angle, and a scanned light beam remains parallel during the course of the scan. Third, differences between the refractive indices of the water, the plastic wall of the cylindrical vessel, and the polymer gel could result in spatial and angular deflections of the laser beam as it passes through the gel vessel. These deflections can be minimized by adjusting the index of refraction of the water by the addition of a material such as propylene glycol or glycerol. In principle, a perfect match would permit acquisition of data over the whole diameter.

Figure 2:
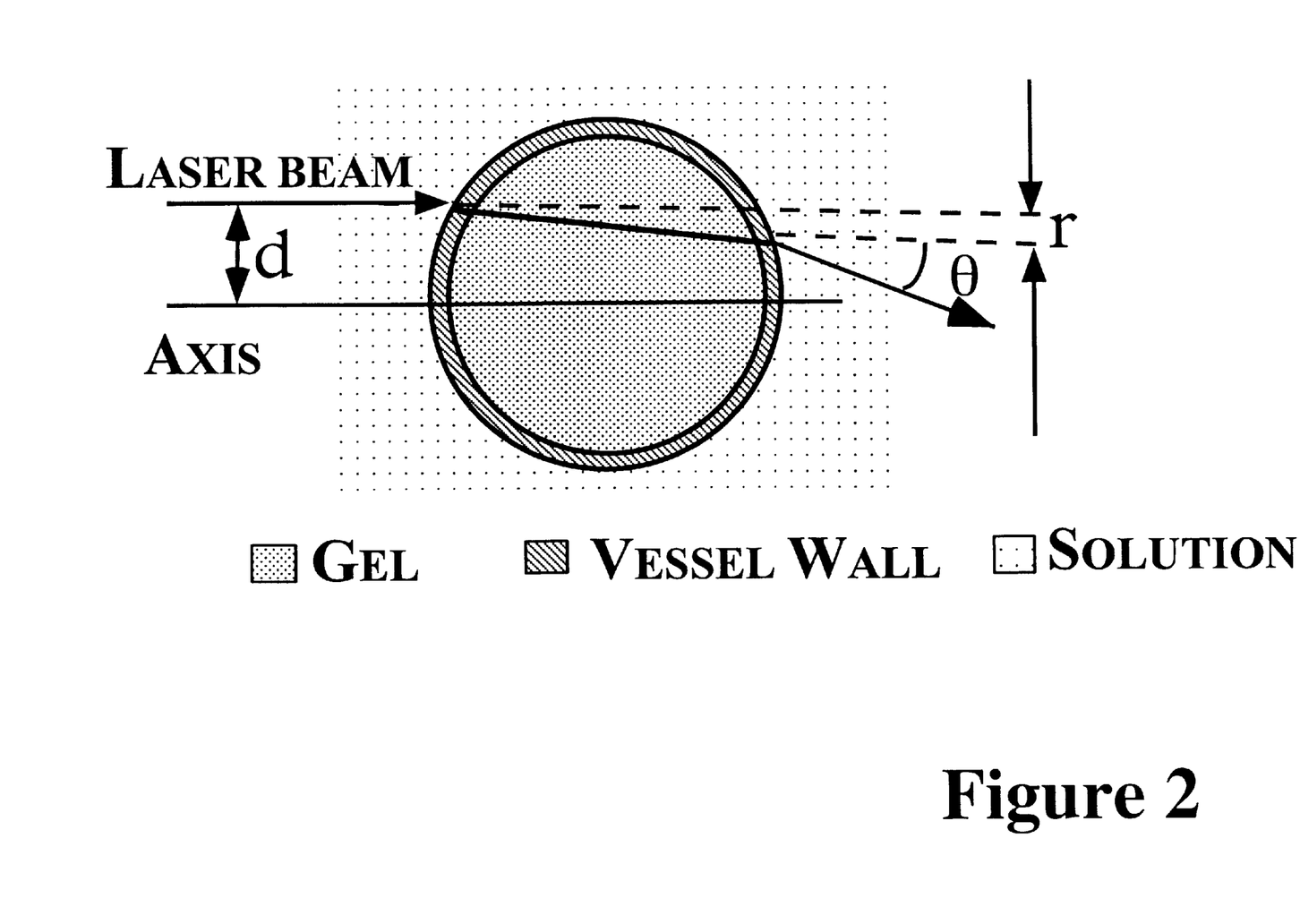
FIG. 2 is a optical geometry diagram showing refraction of the incident laser beam. A computer program is used to calculate the deflection angle θ and deviation r as a function of d and other conditions.
Figure 3:
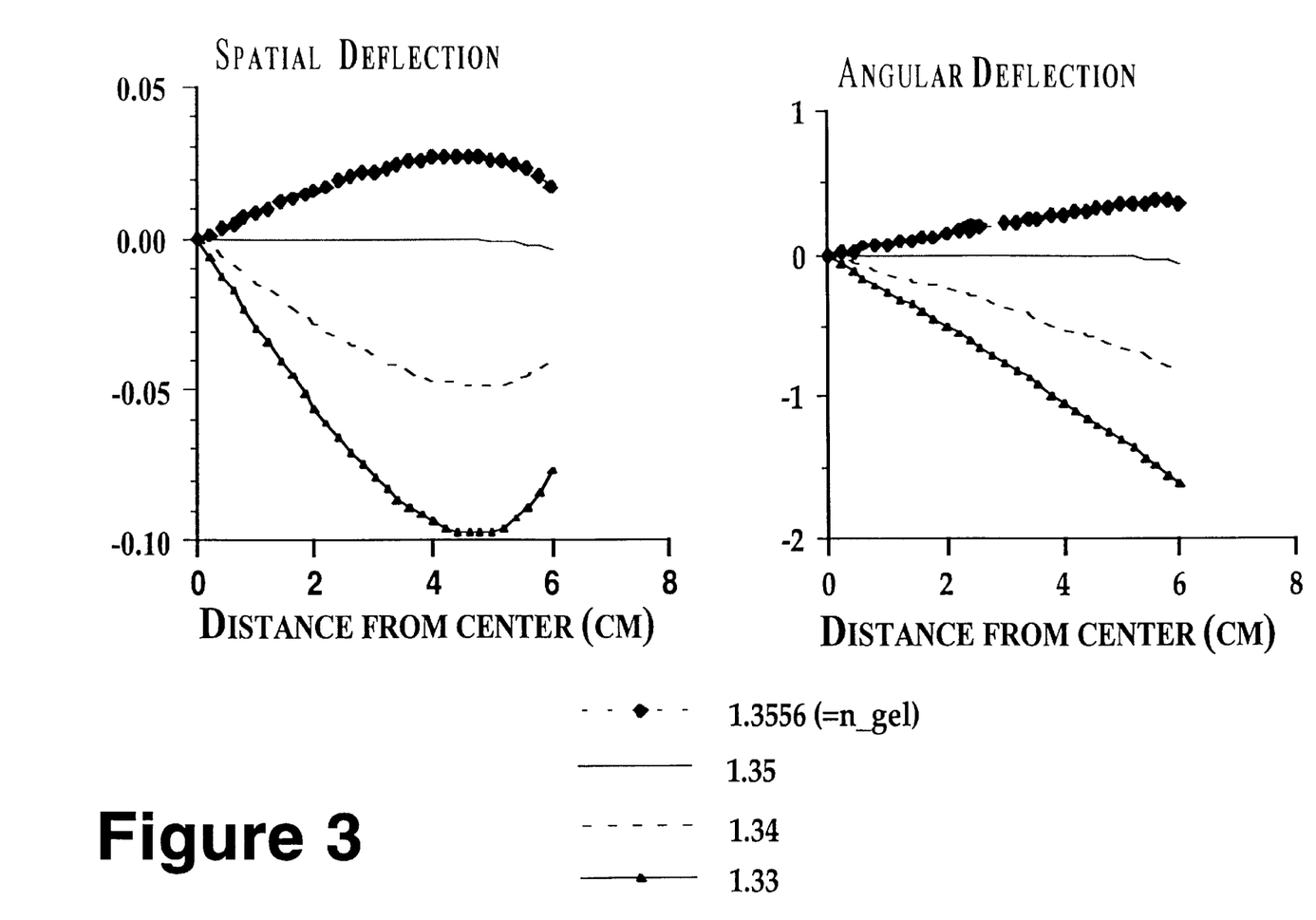
FIG. 3 are graphs showing spatial and angular deflections calculated for different positions in each projection and different refractive indices of the matching solution.

To assess the effects of differences between the indices of refraction of the various components, a computer program was written which calculates beam deviations as a function of distance from the centerline. The geometry analyzed by the program is shown in FIG. 2. The spatial deflection of the laser beam is the vertical distance between the point on the surface of the gel vessel at which the beam actually leaves the vessel and the path of an undeflected beam. The angular deflection is the difference between the direction of the actual beam as it exits the vessel and the direction of an undeflected beam. The computer program calculates the angular and spatial deflections ($\theta$ and r) caused by refraction of the light beam as it passes from the matching solution through the gel vessel, and then back into the solution, for differing indices of refraction of the solution, vessel wall, and gel. FIG. 3 shows the results predicted for a polymer gel held in a Lucite vessel for which the outer radius of the vessel was 6.6 cm, its wall thickness was 3.0 mm, and the refractive index n=1.4893. The value of n for unirradiated gel is 1.3556. As would be expected, the largest spatial and angular deflections occur when the laser beam approaches the edge of the vessel. By matching the index of refraction of the outer chamber solution to that of the gel, and limiting the overall scanning width to 10 cm, distortions of the reconstructed image caused by these deflections can be made negligibly small. This was borne out by comparing the overall point-spread functions for the imaging process at the center and at 4.5 cm from the center, as discussed below.

Prior to imaging irradiated gels, various factors which affect the spatial resolution, dose sensitivity and accuracy of the reconstructed image were evaluated. Spatial resolution in the current system depends upon the diameter of the laser beam, on the mechanical alignment of the scanning laser beam and the axis of rotation of the gel vessel, on backlash in the scanning mechanism, and on the number of projections and the filter employed in the back-projection algorithm. Dose sensitivity and image accuracy depend upon the signal-to-noise ratios of each measurement and the resultant pixel variance in the reconstructed images.

(i) Spatial resolution

Figure 4:
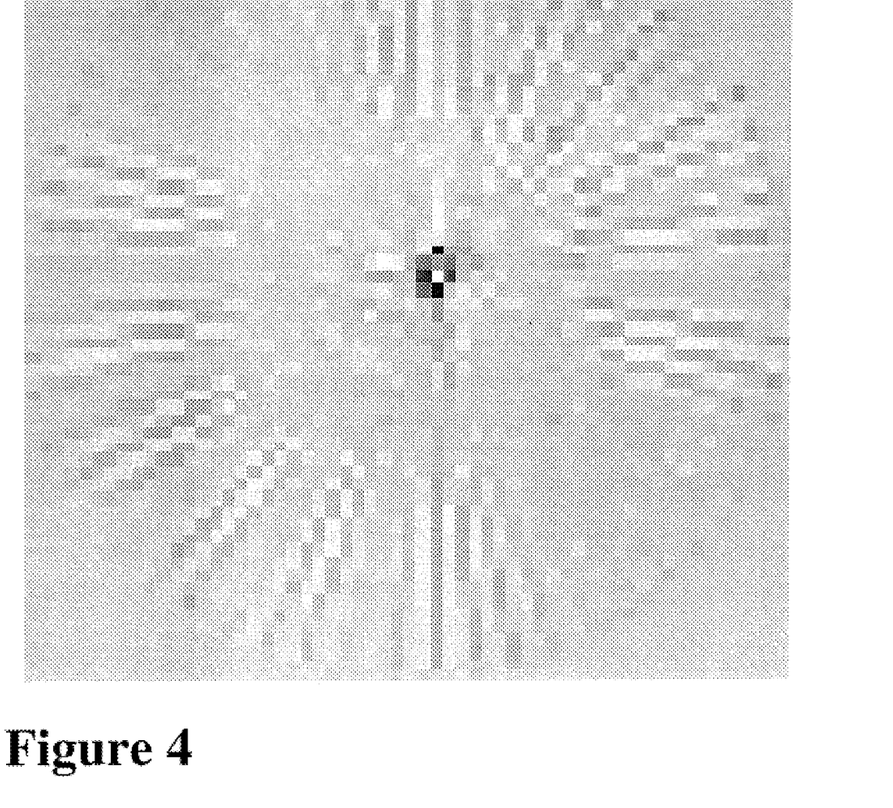
FIG. 4 is a reconstruction of a 0.6 mm tube containing ink. The width of the point spread function is 3.25 mm.

The spatial resolution of the reconstructed image is affected by several factors. These include a) The width (at 1/e of the central maximum) of the laser beam after exiting from the gel is 0.8 mm. Using a laser with a smaller spot size, the effect of beam diameter on spatial resolution can be made insignificant.

b) The back-projection algorithm employed assumes that when the laser beam is at the midpoint of its translational scan it will intercept the axis of rotation of the gel support platform. A misalignment will cause a point to backproject along the tangents to a circle whose diameter depends upon the degree of misalignment. This results in an annular point-spread function and blurring of the image which is a well known phenomenon in conventional axial tomography. The system was aligned by mounting a thin rod on the axis of rotation of the gel platform, and adjusting the translational stage until the shadow of this rod peaked at the midpoint of the scanning width. The overall point-spread function for a 180° rotation of the gel platform was then determined by scanning a thin-walled, 0.6-mm ID capillary tube containing ink. The reconstructed image of this capillary tube had a FWHM of 3.25 mm which is mainly due to residual errors in the mechanical alignment and partly due to the 1.6-mm sampling interval employed. This is shown in FIG. 4. The point-spread function was also obtained from a single scan of the same capillary tube, i.e., with no rotation of the gel platform, assuming all projections are identical, and this had a FWHM of 2.0 mm. These results suggest that a resolution of better than 1 mm should be achievable by employing a smaller diameter laser beam, a more accurate mechanical alignment procedure, and finer sampling of the projection data.

c) By collecting data during both forward and reverse translations of the laser beam, it might be expected that backlash, which occurs when the direction is reversed, would affect image sharpness. However, when scans made with unidirectional motion were compared to those made with the forward/reverse sequence, no differences were detected with a sampling interval of 0.8 mm.

d) The Ram-Lak (ramp), and the Shepp-Logan (sine-apodized ramp) kernels were both used with the back-projection algorithm. The single-scan point-spread function obtained with the Ram-Lak filter had a FWHM of 2.0 mm whereas that obtained with the Shepp-Logan filter was 2.4 mm. The resolution can be increased by taking a higher number of projections and choosing a smaller pixel size.

(ii) Signal to Noise and Image Variance

The minimal detectable change in the optical density for a given pixel size is determined by the signal-to-noise ratio of each sample measurement. With x-ray CT imaging, the primary source of variance in the reconstructed image is due mainly to fluctuations in the signals from the detectors arising from the variance in photon flux (Gore and Tofts, 1978). Systematic variations in the intensity of the beam within a projection are known to give characteristic additional sources of image variance (Tofts and Gore, 1980) but in our system these sources do not appear to be significant when the incident beam intensity is monitored. Random variations in the laser intensity and noise from the detector are negligible. The currently employed laser shows intensity drifts over relatively long times (>>1 minute) of 2% of the mean, but these do not contribute to the inherent noise for each measurement and are corrected by the reference detector. The detectors and preamplifier generate noise, but this can be reduced by averaging samples and by using an appropriate integrating time. The detector used has a sensitive area of 1 $cm^2$. In order to minimize signal fluctuations due to small variations in the locations at which the laser beam impinges upon the detector during the course of scanning, a diffusing window was placed in front of the detector and a 100 mm converging lens is used to correct for lateral shifts. Thus, errors due to beam wandering and possible changes in the detected intensity were minimized.

The variation in reconstructed optical attenuation coefficients was measured by imaging a uniform gel contained ink to increase the optical density above background. With pixels of 1.6 mm by 1.6 mm, 60 projections and using only 10 msec to acquire each data point, the optical attenuation coefficients in the reconstructed image had a standard deviation of 3.5% of the mean. For a uniform gel, the standard deviation of pixels in the reconstructed image corresponded to a dose of 0.051 Gy, which suggests that dose increments of order 0.1 Gy should be reliably detectable at that resolution. When noise-free test data were substituted for experimental data, the resultant image showed a standard deviation of 1.3% for the same matrix parameters. In addition, the noise in the reconstructed images of irradiated gels is reduced substantially when the image of a non-irradiated, uniform gel is subtracted. This demonstrates that a significant fraction of the reconstructed image variance results from the approximate nature of the reconstruction algorithm and limited data sampling rather than from inherent variations in the optical signals.

(iii) Test Results with Polymer Gels.

Figure 5A:
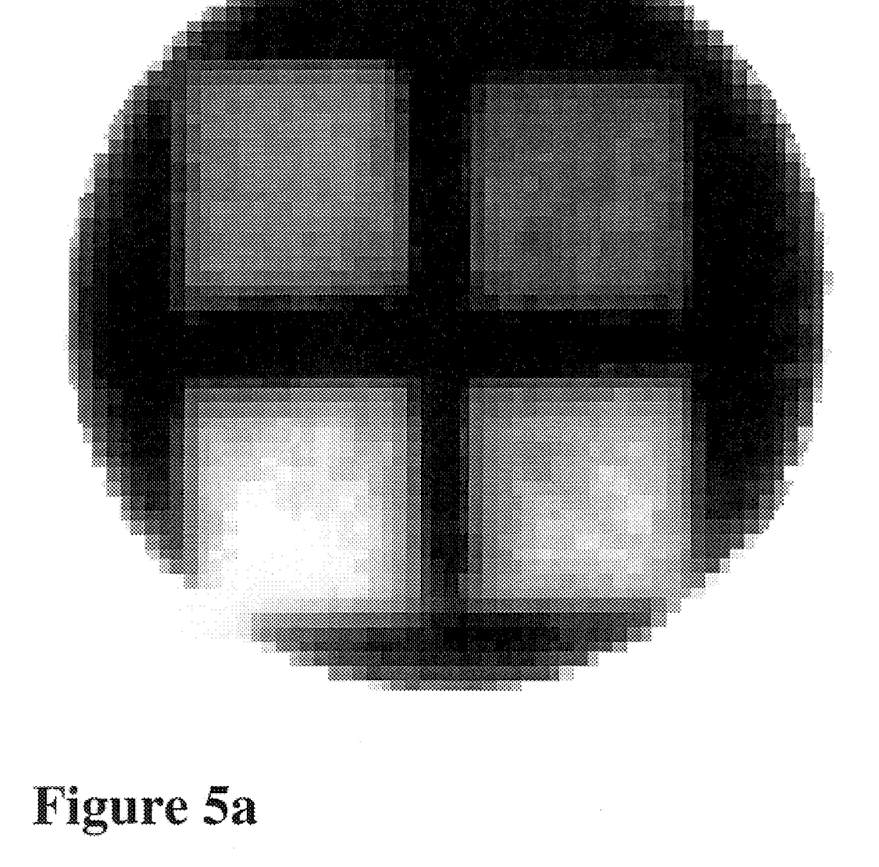
FIG. 5a shows the calculated dose map of a cylindrical sample of radius 10 cms in which 4 rectangular fields of different doses were placed.
Figure 5B:
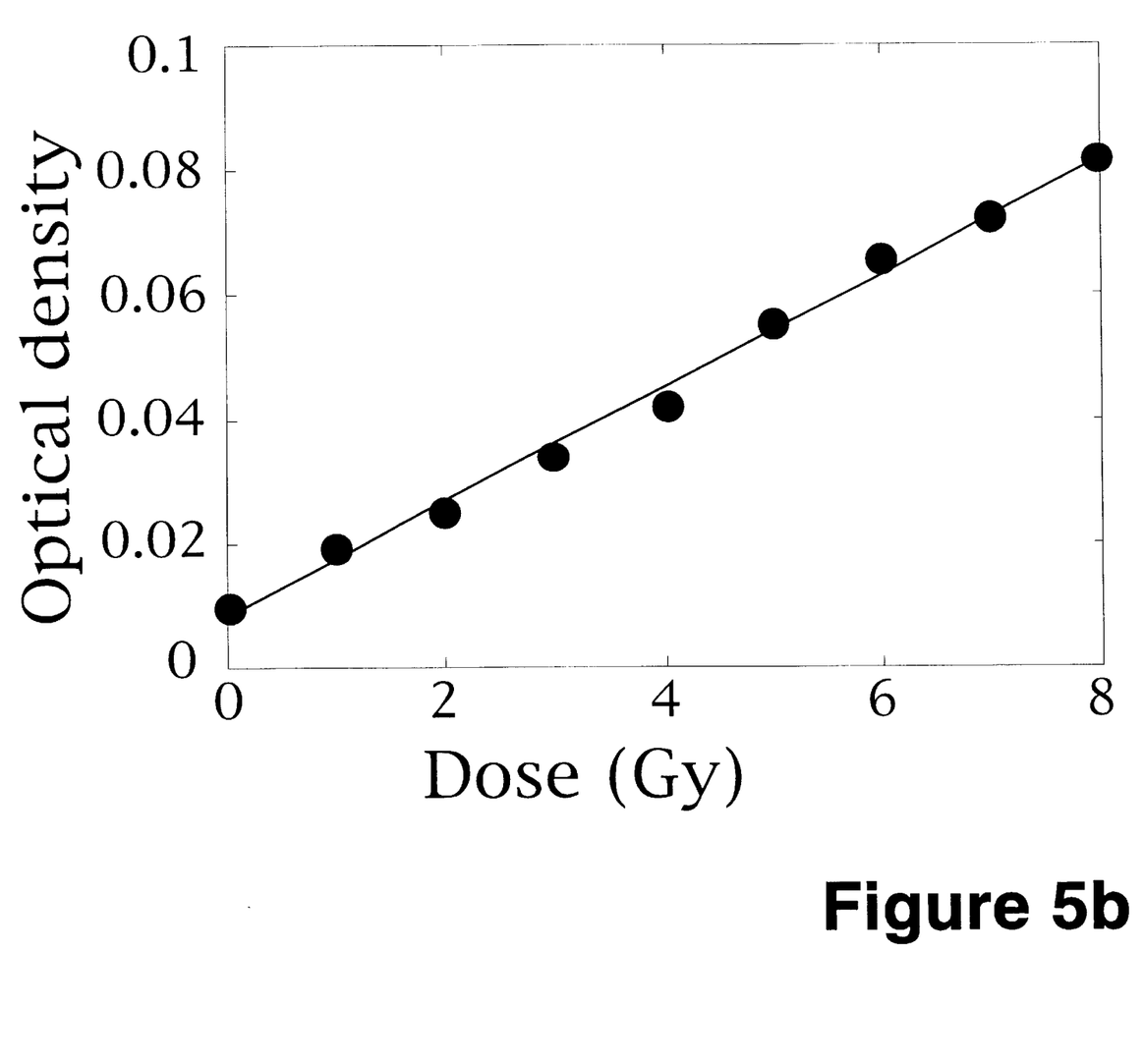
FIG. 5b shows the relationship of optical attenuation per pixel versus dose.

Optically reconstructed images of an irradiated polymer gel are shown in FIG. 5. Four 3×3 $cm^2$ fields of 6 MV x rays were applied through the bottom of a glass volumetric flask. The doses at $d_{max}$ were 5, 6, 7 and 8 Gy, and the flask was scanned at this level. The thickness of the optical section corresponds to the diameter of the laser beam, 0.8 mm, and at $d_{max}$ the dose across this section is essentially uniform. On the lower half of FIG. 5 is a plot of the optical attenuation coefficient versus dose obtained by imaging gels irradiated to known doses. The optical attenuation for 632 nm laser light increases linearly over a wide range of doses, and has a slope 0.63 $mm^{-1}$ per Gy. The slope of this curve depends upon the composition of the gel.

Figure 6A:
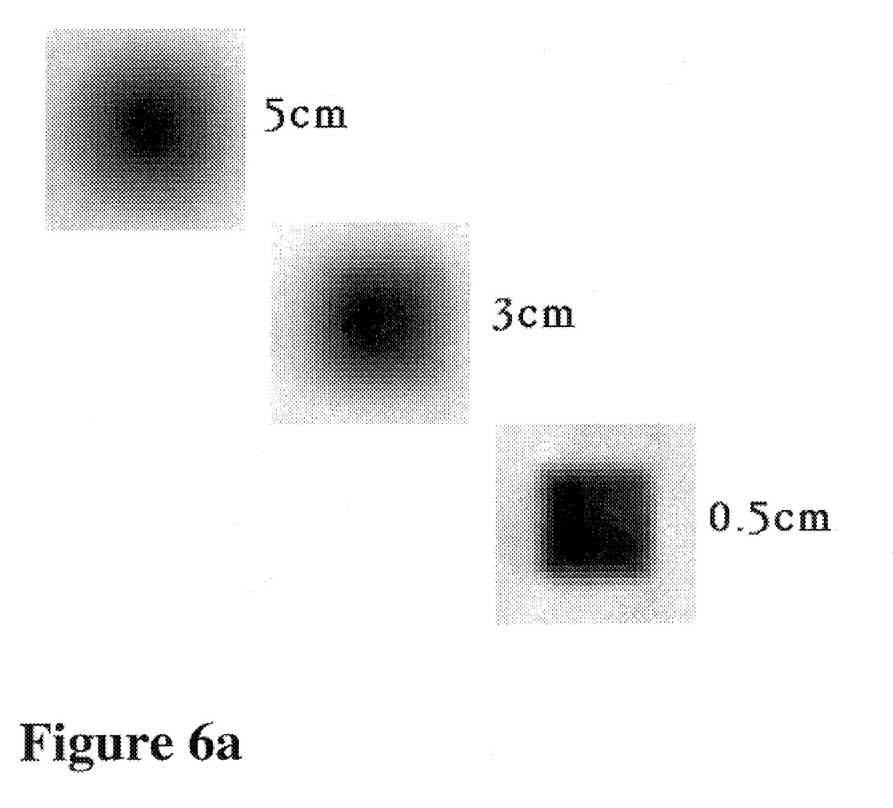
FIG 6a shows the reconstructed images at three depths (0.5, 3 and 5 cm).
Figure 6B:
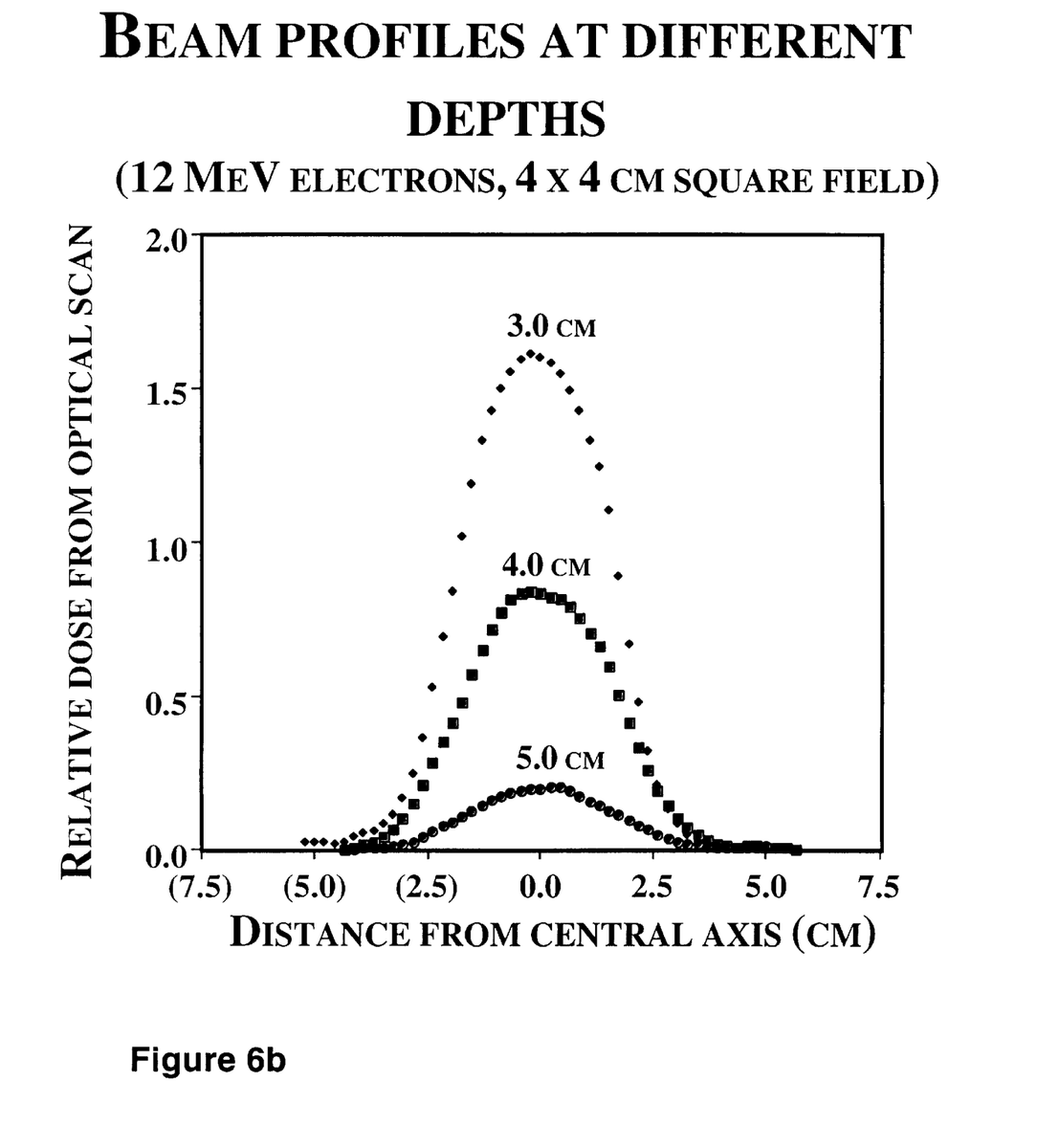
FIG 6b shows cross sectional profiles of the dose variation across three fields (at 3, 4 and 5 cm depth).

FIG. 6a shows the reconstructed images of a 12 MeV, 4×4 $cm^2$, electron beam measured at depths of 0.5 cm, 3.0 and 5.0 cm. Plots of the dose variations across slices at 3, 4 and 5 cm depth are shown in FIG. 6b.

Brachytherapy sources can be inserted and the gels can be scanned afterwards as long as the void provided for the source is filled with optically matched material. The prototype device described here uses low cost components and the simplest form of optical scanning, and clearly there are improvements that can be made to the performance. The major current impediment to decreasing data acquisition time is the linear translation speed of the carriage that carries the two mirrors. The major limitations currently on resolution are the spot size of the scanning laser beam, the resolution matrix used in preliminary work, and the accuracy of alignment of the center of rotation. These may all be improved to significant degrees with further development of the method and apparatus. A sampling interval of less than 1 mm is easily achieved, while the number of projections used determines the time of scanning but can be increased to the limit permitted by the angular resolution of the stepping motor (a fraction of one degree). The noise in the reconstructed image is currently limited by numerical approximations, the small number of projections used, and the performance of the detector. Increasing the number of projections, and post-processing will reduce the image variance. The optical attenuation and dose in a volume element of approximately 2 $mm^3$ can be estimated to within 5% using the current system. Optical scanning in conjunction with polymer gels provides an effective alternative to MRI/gel systems, and that it will have a useful role in radiation physics practice.

Although the examples provided herein are for gel-based systems, it is understood that other translucent media may also be used so long as they are relatively dimensionally stable in three dimensions. Similarly, although the measured optical attenuation is attributable to scattering by the polymerized monomer other reactants may be used in the translucent media which under influence of an energy field produce localized changes in optical density. For example, reactants which change color upon exposure to an energy field may be used to vary optical attenuation of a laser by absorption are within the scope of this invention.

The invention thus provides an optical scanner for measuring three dimensional dosimetric data comprising a translucent medium exhibiting optical properties which change upon receipt of radiant energy representing a dose distribution of the energy, such as optical density, light scattering, emitted light intensities, light speeds, and combinations thereof; at least one light beam for scanning the translucent medium; and at least one detector for receiving and measuring data indicative of changes in the optical properties of the medium after scanning from multiple directions to provide a representation of the optical properties in sections through the medium.

The light beam is typically a laser beam or a series of divergent rays, including not only light produced by point sources but also thin sheets of light such as that provided by a laser diode line generator. Light beams in some embodiments may be moved so that they create parallel rays through the medium, but arc scans may be employed in other embodiments. The geometry and/or selection of medium, and the materials comprising a container for housing the medium where one is employed, are selected so that the light beam passes through the space that is scanned in straight lines (without refraction and/or reflection) in some embodiments.

In illustrative examples described above, moving mirrors are employed to deflect light beams to provide scanning from multiple directions, but alternate embodiments utilize movement of the space accommodating the medium, movement of one or more detectors, and/or movement of the light beam. Thus, medium positioning, light beam reorientation, detector movement, and combinations of any of these may be employed in the practice of the invention to provide data needed to reconstruct three-dimensional energy fields. For example, the beam and detectors may be fixed and the sample, rotated, or the beam and sample are fixed, and the detectors, rotated. However, internal movement of scanner portions are not necessary in embodiments employing arrays of multiple detectors that surround the sample and/or multiple light beams, so long as data indicative of changes in optical properties from different angles are provided so that a reconstruction can be made from a series of projections of the optical properties. Multiple detectors include arrays of detecting elements. A collimating aperature, including slits, holes, and series of holes, that limits the light detected by a detector may be used in some embodiments.

The invention further provides a method of reconstructing a three-dimensional energy field as a series of two-dimensional images comprising the steps of applying an energy field to a translucent medium having distinct optical properties that change upon receipt of the energy field; optically scanning the translucent medium at various angles; detecting and measuring data indicative of optical changes in the medium; and preparing a two-dimensional image of the energy field by analyzing the changes in the optical properties. Methods of the invention are particularly adapted to radiant energy fields. By "radiant energy" is meant any radiation, particualrly that used in medical and cancer treatment, including visible, UV, and IR light, x-rays, acoustic fields, particle beams such as high energy electron beams, and the like which can be used to produce measureable changes in the optical properties of a translucent medium subjected to radiant energy.

Any translucent medium that is not opaque may be scanned using the apparatus and method of the invention, including transparent media and mixtures of transparent and translucent materials. Media containing a reactant which changes upon receipt of radiant energy representing a dose distribution may also be employed in some embodiments. As illustrated above, example media include polymeric gels and gels containing radiochromic dye. In some medical embodiments, the translucent medium is tissue equivalent, and the radiant energy field produces a dose equivalent.

Typical optical scanners and methods include a microprocessor for combining the optical data into the two-dimensional images, for example, using the methods of reconstruction from projections developed for computer tomography. Some methods of the invention include steps related to changing the depth of the translucent medium at which the optical scanning step occurs, and repeating the optical scanning and detecting steps to provide other two-dimensional images. In some embodiments, the two-dimensional images are reviewed in consideration of altering or confirming radiant energy treatments.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

REFERENCES

Gore, J. C., and Tofts, P. S., 1978, Statistical limitations in computed tomography, *Phys. Med. Biol.*, 23, 1176–1182.

Maryanski, M. J., Gore, J., and Schulz, Three-Dimensional Detection, Dosimetry and Imaging of an Energy Field by Formation of a Polymer in a Gel, U.S. Pat. No. 5,321,357 (Jun. 14, 1994).

Maryanski, M. J., Schulz, R. J., Ibbott, G. S., Gatenby, J. C., Xie, J., Horton, D., and Gore, J. C., 1994, Magnetic resonance imaging of radiation dose distributions using a polymer-gel dosimeter, *Phys. Med. Biol.* 30, 1437–1455.

Maryanski, M. J., G. S. Ibbott, Eastman, P., Schulz, R. J., and Gore, J. C., 1995, Radiation therapy dosimetry using magnetic resonance imaging of polymer gels. *Med. Phys.* 23, 699–705.

Ramachandran, G N, and Lakshminarayanan, A V, 1971, Three dimensional reconstruction from radiographs and electron micrographs: applications of convolutions instead of Fourier transforms, *Proc. Natl Acad. Sci. USA*, 68, 2236–40.

Shepp, L. A. and Logan, B. F., 1974, The Fourier reconstruction of a head section, *IEEE Trans. Nucl. Sci.*, NS-21, 21–43.

Tofts, P. S., and Gore, J. C., 1980, Some sources of artefact in computed tomography. *Phys. Med. Biol.* 25, pp. 117–127.

The above patent and papers are hereby incorporated herein in their entireties by reference.

What is claimed is:

1. A method of imaging and measuring a three-dimensional dose distribution of an energy field in a translucent, three-dimensional object comprising the steps of:
    applying an energy field to the object such that the optical properties are changed upon receipt of the energy;
    optically scanning the object at various angles;
    detecting and measuring light projection data indicative of optical changes in the object;
    calibrating the optical change in the object to the dose of the energy; and
    mapping the dose of the energy in the object.

2. A method according to claim 1 wherein the translucent object is tissue equivalent material.

3. A method according to claim 1 wherein the translucent object comprises polymer gels.

4. A method according to claim 1 wherein the translucent object comprises a gel containing radiochromic dye.

5. A method according to claim 1, wherein the energy field is applied in radiation therapy and the data is reviewed in consideration of altering or confirming radiant energy treatment.

6. A method according to claim 1, wherein the energy field that changes optical properties of the object is light.

7. A method according to claim 1, wherein the energy field that changes optical properties of the object comprises x-rays or charged particles.

8. A method according to claim 1, wherein the energy field is acoustic.

9. A method according to claim 2, wherein the energy field is applied in radiation therapy for the purpose of assessing the dosimetry or quality assurance of the therapy.

10. An optical tomographic scanner for imaging optical properties of translucent three-dimensional objects, comprising:
    at least one light source for illuminating the object;
    at least one light detector for measuring light that has interacted with the object;
    a mechanism that controls the relative motion of the object, the light source or sources, and the light detector or detectors;
    a tank filled with a liquid in which the object is immersed for refractive index matching, so that the light rays passing through the object are propagated in straight lines; and
    a computer for controlling the scanner mechanism and for calculating the three dimensional distribution of optical properties inside the object.

11. An optical scanner according to claim 10, wherein a single detector is used.

12. An optical scanner according to claim 10, wherein the object rests on a turntable that rotates inside a tank that is filled with a refractive index-matching liquid.

13. An optical scanner according to claim 10, wherein the optical properties of the object are measured in the visible region of the light spectrum.

14. An optical scanner according to claim 10, wherein the optical properties of the object are measured in the ultraviolet region of the light spectrum.

15. An optical scanner according to claim 10, wherein the optical properties of the object are measured in the infrared region of the light spectrum.

16. An optical scanner according to claim 10, wherein the optical properties measured are selected from the group consisting of light absorption, light scattering, light emission, light refraction, light speed, and combinations thereof.

17. An optical scanner according to claim 10, wherein the light source and the light detector are moved in parallel straight lines on opposite sides of the tank.

18. An optical scanner according to claim 10 wherein the light source is laser light.

19. An optical scanner according to claim 10 wherein multiple detectors or a detector comprising an array of detecting elements are employed.

20. An optical scanner according to claim 10 wherein moving mirrors are employed to deflect light beams to provide scanning from multiple directions.

* * * * *